(12) United States Patent
Stine et al.

(10) Patent No.: US 9,125,529 B2
(45) Date of Patent: Sep. 8, 2015

(54) WATER-POWERED HAND-WASHING SYSTEM

(71) Applicant: Clean Hands, Inc., Whiting, VT (US)

(72) Inventors: Patrick Stine, Whiting, VT (US); Aaron G. Loomis, Huntington, VT (US); Paul C. Henninge, Burlington, VT (US)

(73) Assignee: CLEAN HANDS, INC., Whiting, VT (US)

( * ) Notice: Subject to any disclaimer, the term of this patent is extended or adjusted under 35 U.S.C. 154(b) by 0 days.

(21) Appl. No.: 14/328,910

(22) Filed: Jul. 11, 2014

(65) Prior Publication Data
US 2015/0000030 A1 Jan. 1, 2015

Related U.S. Application Data

(60) Continuation-in-part of application No. 13/683,597, filed on Nov. 21, 2012, now abandoned, which is a continuation-in-part of application No. 13/223,459, filed on Sep. 1, 2011, now Pat. No. 8,337,633, which is a division of application No. 12/371,673, filed on Feb. 16, 2009, now Pat. No. 8,028,710.

(60) Provisional application No. 61/056,546, filed on May 28, 2008.

(51) Int. Cl.
| | |
|---|---|
| *B08B 6/00* | (2006.01) |
| *B08B 3/00* | (2006.01) |
| *A47K 7/04* | (2006.01) |
| *A61H 35/00* | (2006.01) |
| *A61B 19/00* | (2006.01) |
| *E03C 1/04* | (2006.01) |
| *A45D 29/17* | (2006.01) |

(52) U.S. Cl.
CPC . *A47K 7/04* (2013.01); *A61B 19/36* (2013.01); *A61H 35/00* (2013.01); *E03C 1/04* (2013.01); *A45D 29/17* (2013.01); *A61H 2205/067* (2013.01)

(58) Field of Classification Search
None
See application file for complete search history.

(56) References Cited

U.S. PATENT DOCUMENTS 2,223,204 A * 11/1940 Carmichael ............... 132/73
2,747,588 A   5/1956 Bonner
(Continued)

FOREIGN PATENT DOCUMENTS

| EP | 0389884 | 10/1990 |
|---|---|---|
| FR | 2758445 | 7/1998 |

OTHER PUBLICATIONS

Meritech, 500EZ Product Information Sheet, www.meritech.com/products/500/index.php.

*Primary Examiner* — Eric Golightly
*Assistant Examiner* — Arlyn I Rivera-Cordero
(74) *Attorney, Agent, or Firm* — Occhiuti & Rohlicek LLP

(57) ABSTRACT

A hand-washing apparatus configured to simultaneously wash hands includes an enclosure with openings for each hand, and members for finger support and thumb support. The finger support member extends upward from the enclosure's base and the thumb support member extends along a direction different from the finger support member. The finger support has a surface for receiving and orienting fingers of both hands at corresponding locations inside the enclosure. Similarly, the thumb support has a surface for receiving and orienting both thumbs. The finger-support surface has two recess sets, each of which receives fingers of one hand. First and second spray-nozzles are directed to irrigate the fingers and thumbs respectively.

20 Claims, 12 Drawing Sheets

(56) References Cited

U.S. PATENT DOCUMENTS

| | | |
|---|---|---|
| 3,982,965 A | 9/1976 | Spotz |
| 4,020,856 A | 5/1977 | Masterson |
| 4,119,439 A | 10/1978 | Boucher |
| 4,137,929 A | 2/1979 | Grossman |
| 4,289,152 A | 9/1981 | Fuhre |
| 4,635,656 A | 1/1987 | Daniel |
| 4,742,836 A | 5/1988 | Buehler |
| 5,085,234 A * | 2/1992 | Silverman .................. 132/73 |
| 5,193,563 A | 3/1993 | Melech |
| 5,522,411 A | 6/1996 | Johnson |
| 5,713,378 A | 2/1998 | Smith |
| 5,755,240 A | 5/1998 | Schonborn |
| 5,823,447 A | 10/1998 | Maybach |
| 6,176,941 B1 | 1/2001 | Jewett et al. |
| 6,431,189 B1 | 8/2002 | Deibert |
| 2005/0081291 A1* | 4/2005 | Otten .................. 4/621 |
| 2009/0293913 A1 | 12/2009 | Stine |
| 2009/0299787 A1 | 12/2009 | Barnhill |

* cited by examiner

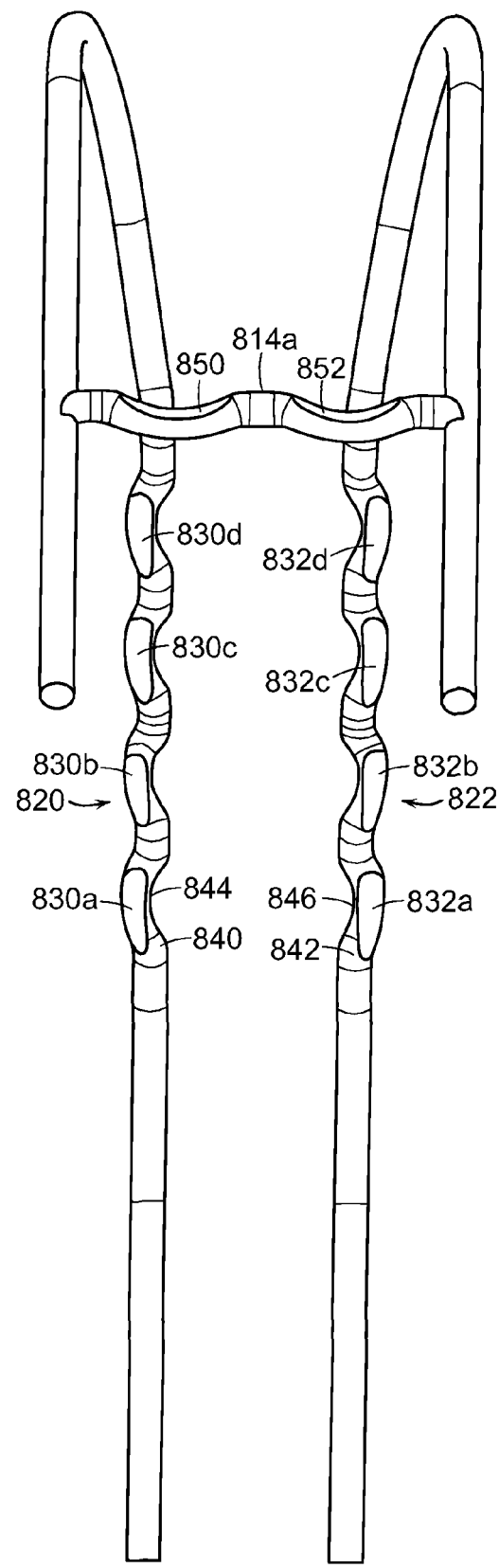

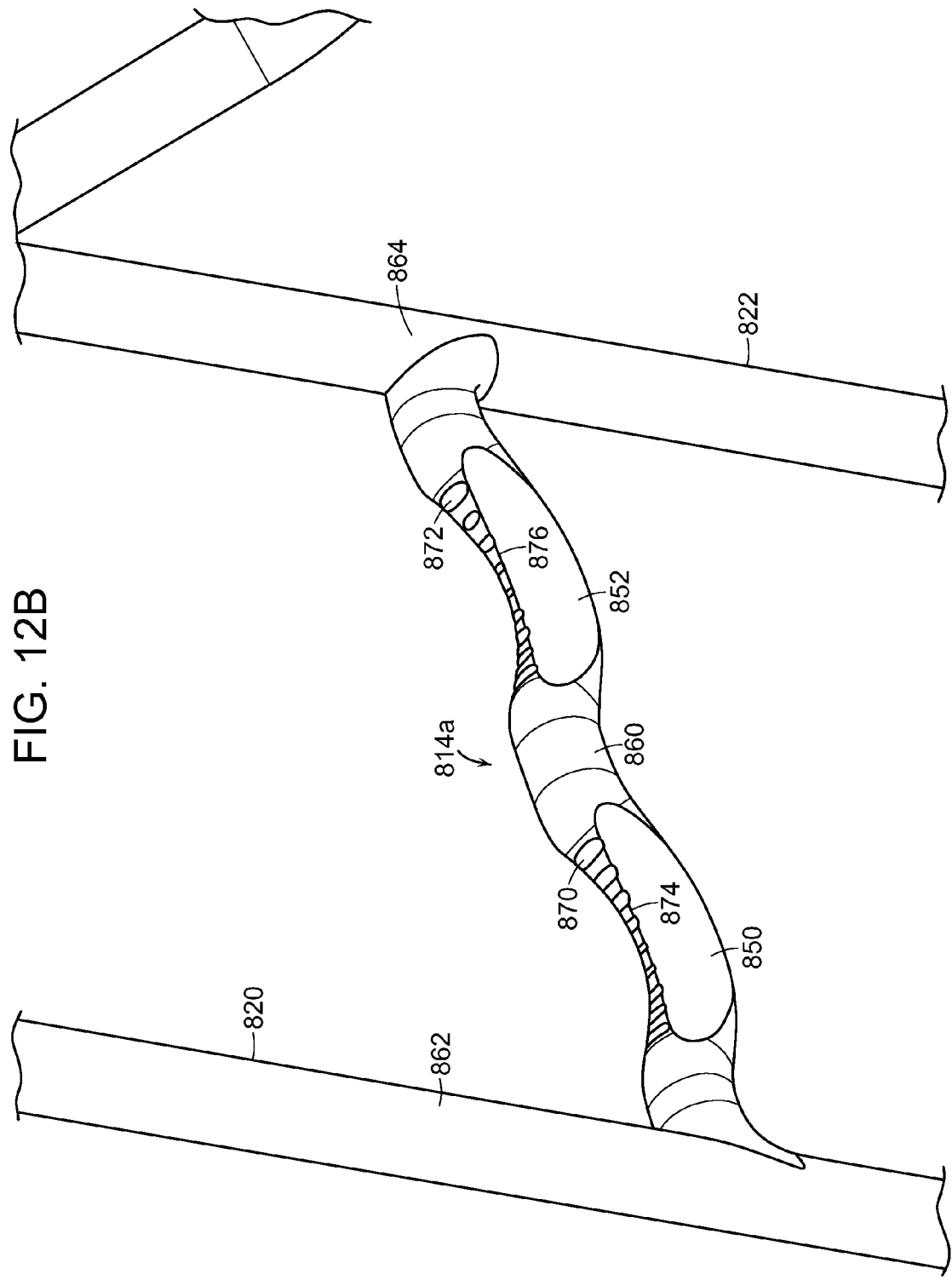

WATER-POWERED HAND-WASHING SYSTEM

RELATED APPLICATION DATA

This application is a continuation-in-part of non-provisional U.S. application Ser. No. 13/683,597, filed Nov. 21, 2012 and issued as U.S. Pat. No. 8,337,633 on Dec. 25, 2012, which is a continuation-in-part of non-provisional U.S. application Ser. No. 13/223,459, filed Sep. 1, 2011, which is a divisional of U.S. application Ser. No. 12/371,673, filed Feb. 16, 2009 and issued as U.S. Pat. No. 8,028,710 on Oct. 4, 2011, and titled "Water-Powered Hand-Washing System and Method," which is incorporated by reference herein in its entirety. This application also claims the benefit of priority of U.S. Provisional Patent Application Ser. No. 61/056,546, filed on May 28, 2008, and titled "Water-Powered Handwasher And Hand-Washing Method," which is incorporated by reference herein in its entirety.

FIELD OF THE INVENTION

The present invention generally relates to the field of personal hygiene. In particular, the present invention is directed to a method of hand-washing using a hand-washing system.

BACKGROUND

All human surfaces harbor bacteria; some have favorite places. Certain forms of non-pathogenic streptococci limit their homesites to the first millimeter of oral mucosa at the gumline. Common forms of *staphylococcus* are found in a third of asymptomatic noses. By virtue of their role in touching public items, procuring food, picking noses, satisfying itches and handling-the-paper chores, the thumb and first two fingers probably provide the greatest sample and volume of bacteria from the daily environment. If those digits carry pathogenic *E. coli, Salmonella* or methicillin-resistant Staph *aureus* (MRSA), you may have a major health problem. If they invite more ordinary bacteria and viruses to the kitchen and dinner table, you may just get sick for a few days.

One way to stay healthy is to reduce the bacterial count on the hands. It is impossible, even with a ten-minute surgical scrub, to eliminate all of them. A unique problem exists in the nail beds, where accumulated oil and dirt may provide a refuge for bacteria and be hard to displace. Soaps and detergents act in two ways. Their main role is to cut the grease and soften the buildup under the nails and in the cuticles. They may also directly injure the cell membranes of bacteria, affecting their mobility or even killing them. Soaps and detergents require sufficient time and concentration at the work site to be effective.

Commonly used bactericidal chemicals intended for use on skin, for example, antiseptics, include iodine and mercury compounds, phenol, alcohol, benzalkonium chloride, mineral spirits, propylene glycol, chlorhexidine and hexachlorophine. Their role in routine hand cleaning is limited by their potential to irritate skin.

A number of devices have been developed over the years for assisting in the cleaning of fingertips, particularly the hard-to-clean nail beds and cuticles. However, each of these devices has at least one drawback, ranging from low cleaning efficiency to difficulty in cleaning the device between uses, among others.

SUMMARY OF THE DISCLOSURE

The invention includes a hand washing apparatus configured to simultaneously wash both a left hand and a right hand, comprising, an enclosure having an exterior surface and an interior space, the exterior surface having a front face and first and second side faces located on opposites sides of the front face. The enclosure includes a first opening in the first side face of the exterior surface for receiving a left hand for insertion into the interior space and a second opening in the second side face of the exterior surface for receiving a right hand for insertion into the interior space. There is first digit support member located within the interior space having a surface for receiving and orienting a first subset of digits of the first and second hands in a predetermined position within the interior space and a second digit support member located within the interior space having a surface for receiving and orienting a second subset of digits of the first and second hands in a predetermined position within the interior space. There is a first spray nozzle, positioned in the interior space and directed toward the first digit support member at a first predetermined orientation, configured to spray a liquid toward the first subset of digits of the first and second hands when the hands are inserted into the interior space. There is also a second spray nozzle, positioned in the interior space and directed toward the second digit support member at a second predetermined orientation, configured to spray a liquid toward the second subset of digits of the first and second hands when the hands are inserted into the interior space. The first and second subsets of digits comprise all of the digits of the left and right hands.

In another aspect of this invention, the first digit support member includes at least one surface with a plurality of recesses to receive the first subset of digits of the left and right hands and the second digit support member includes a surface to receive the second subset of digits of the left and right hands. The surface of the second digit support member includes a plurality of recesses to receive the second subset of digits of the left and right hands. The first digit support member includes a plurality of concave surfaces one associated with each of said plurality of recesses and wherein at an intersection of each concave surface and its associated recess is formed a curved edge for engaging with a digit of the first subset of digits.

In a further aspect of this invention, the second digit support member includes a plurality of concave surfaces one associated with each of said plurality of recesses and wherein at an intersection of each concave surface and its associated recess is formed a curved edge for engaging with a digit of the second subset of digits. The plurality of recesses in the second digit support member includes a surface having one of a coating and an increased roughness to increase the friction of the surface. Each of the plurality of recesses in the first digit support member includes a surface having one of a coating and an increased roughness to increase the friction of the surface. The first digit support member includes two surfaces, a first surface for receiving the digits of a right hand and a second surface for receiving the digits of the left hand. The first digit support member includes first and second support elements, said first support element includes said first surface for receiving the digits of the right hand and said second support element includes said second surface for receiving the digits of the left hand.

In yet another aspect of this invention, the first subset of digits includes the three-phalanx digits and the second set of digits includes the two-phalanx digits. The first digit support member orients the first subset of digits in an upward facing direction toward an upper wall of the interior space and the second digit support member orients the second set of digits in a rearward facing direction toward a rear wall of the interior space. The first spray nozzle is located proximate an upper wall of the interior space and is directed toward the first subset of digits and wherein the second spray nozzle is located proximate a rear wall of the interior space and is directed toward the second subset of digits. The second spray nozzle is angled at approximately 20 degrees upward relative to a horizontal plane perpendicular to the rear wall and the first spray nozzle is angled at about 115 to 120 degrees from the second spray nozzle.

The invention also includes first and second openings which are spherical in shape and have curled lip portions angled inward toward the interior space on an upper portion of the openings and curled lip portions angled outward away from the interior space on a lower portion of the openings. There is a drain located in a bottom wall of the interior space for allowing sprayed liquid to be removed from the interior space and a sensor to activate a cleaning cycle when the hands are placed in the interior space.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 10b is a front isometric view of the embodiment of the two hand work enclosure of a water-powered hand-washing system of FIG. 10a.

FIG. 12a is a front isometric view of the digit support members according to this invention for supporting all of the user's fingers.

FIG. 12b is a front isometric view of the digit support member according to this invention for supporting the user's thumbs.

DETAILED DESCRIPTION

The present disclosure is directed to water-powered hand-washing systems and components therefor that provides significant advantages over conventional water-based hand-washing devices known to the present inventor. Important among these advantages is the fact that a hand-washing system of the present disclosure provides excellent cleaning effectiveness, especially in the ability to dislodge and remove large fractions of bacteria and other foreign matter from fingernail beds and cuticular regions of fingers and thumbs with relatively little effort on the user's part, as compared to conventional cleaning methods, such as scrubbing with a nail brush. Another important advantage is that this cleaning effectiveness can be achieved at conventional domestic water supply pressures, for example, from about 20 pounds per square inch (PSI) to about 50 PSI. Other important advantages and improvements over conventional hand-washing devices, systems and methods will become apparent upon reading the following disclosure.

Figure 1:
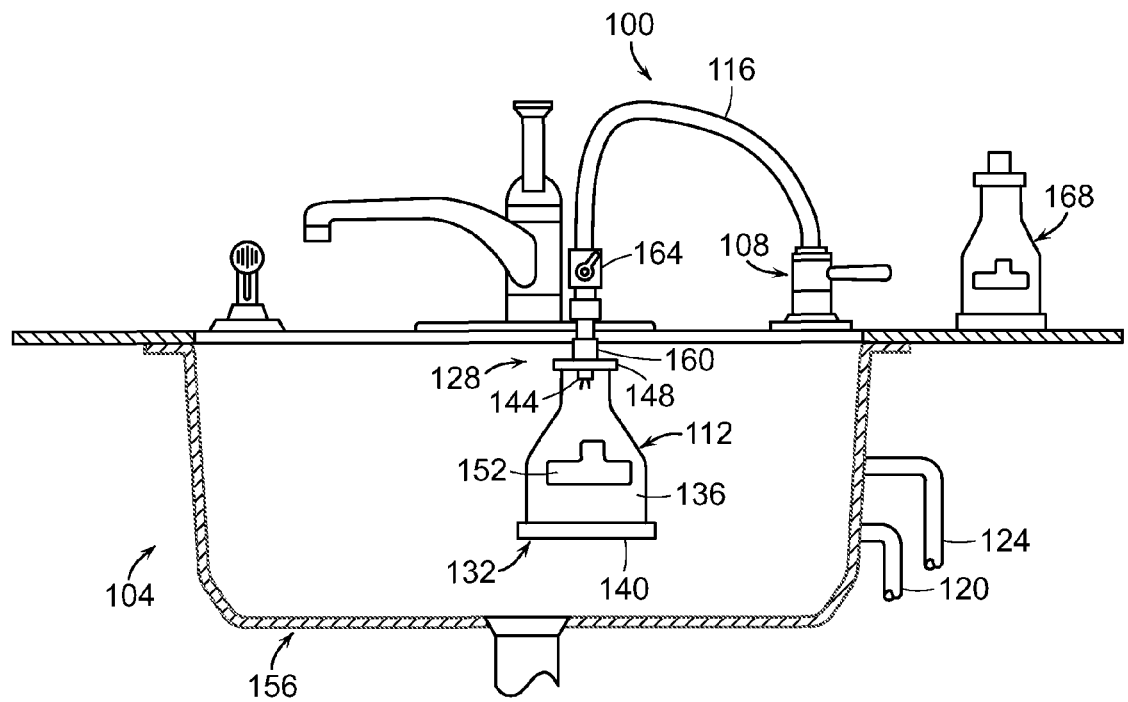
FIG. 1 is a partial cross-sectional view/partial elevational view of a water-powered hand-washing system installed in a household kitchen sink setting.

Turning now to the drawings, FIG. 1 illustrates an example of a water-powered hand-washing system 100 made in accordance with broad concepts disclosed herein. In this example, hand-washing system 100 is shown in a home-kitchen environment wherein it is integrated into a kitchen-sink installation 104. As such, hand-washing system 100 is readily available for use by virtually all members of the corresponding household, except perhaps for the very youngest of children. Installing a hand-washing system of the present disclosure in a central location, such as in a kitchen, is desirable because in some embodiments an important aspect of the system is that it be used routinely by all members of the household throughout the day, especially following any activity, such as gardening and preparing meals from raw meat, in which fingernail beds and cuticular regions become particularly dirty and/or are exposed to bacteria-laden/bacteria-promoting matter and especially before engaging in an activity, such as eating and dental flossing, where any bacteria and/or other undesirable matter present in fingernail beds and cuticular regions could easily enter a human body.

As those skilled in the art will readily appreciate, a home-kitchen environment, such as installation 104 of FIG. 1, is only one example of a location suitable for containing a water-powered hand-washing system made in accordance with one or more of the broad concepts of the present disclosure. Other examples of environments where installation of a system of the present disclosure would be beneficial include, but are not limited to, commercial kitchen environments to assist in the cleaning of hands of cooks and other food handlers so as to inhibit the spread of bacteria and other undesirable matter among food items and work areas, and health care environments to assist surgeons, physician's assistants and nurses in preparing for surgery or providing hands-on patient care so as to reduce the likelihood of contaminating the patient and risking infection. Indeed, and as described below, some of the broad concepts of the present disclosure are directed to features that will contribute to the efficacy of such systems not only in home and kitchen use, but in use in surgical settings where the cleanliness requirements are much more critical. Some or all of these features are lacking in various ones of conventional finger/thumb/hand cleaning assistance devices of which the present inventor is aware.

With continuing reference to FIG. 1, primary components of hand-washing system 100 include a mixing/flow valve 108, a work enclosure 112 and a flexible conduit 116 that fluidly connects the work enclosure to the mixing valve. Mixing/flow valve 108 is fluidly connected to each of a cold water supply line 120 and a hot water supply line 124, which may be any conventional domestic water supply lines, such as half-inch household lines that typically deliver a maximum of 1.8 gallons per minute (GPM) (California plumbing regulations) to 2.5 GPM (the rest of the U.S.) within a range of 20 PSI to 60 PSI. Typically, the hydrostatic pressure available in household water lines ranges from 20 PSI to 50 PSI, with an average range of about 35 PSI to 45 PSI in most municipal lines and 35 PSI to 40 PSI in most well or domestic, pump-driven lines.

When in use, mixing/flow valve 108 mixes cold and hot water from, respectively, cold and hot water supply lines 120, 124 so as to provide a desired/suitable temperature to the mixed output water, which flexible conduit 116 then provides to work enclosure 112. A thermostatic cartridge with mixing/flow valve 108 can protect users from scalding by limiting the maximum hot water temperature provided. Mixing/flow valve 108 also allows a user to adjust the flow of water provided to work enclosure 112 so as to optimize the cleaning conditions and user comfort of the spray within the enclosure. Mixing/flow valve 108 may be any suitable mixing valve. An example of a suitable mixing valve is the mixing valve portion of the Kohler® HIRise™ sidespray unit model K-7344-4, available from Kohler Company, Kohler, Wis. Of course, that unit would have to be modified to receive flexible conduit 116 rather than the sidespray assembly accompanying the valve. In a particular example, the modified unit includes flexible conduit 116 in a length of 28 inches measured from the base at the countertop to the shutoff valve (164). Of course, any one of many other mixing valves could be used. A constraint on the choice of mixing valves for use as mixing valve 108 is that the selected valve must be able to provide the water pressures and flow rates described below that are needed to provide hand-washing system 100 with it cleaning effectiveness.

As will become apparent from reading the following description, during use work enclosure 112 is designed to be oriented as shown in FIG. 1. As such, during use work enclosure 112 has an upper end 128 and a lower end 132. Primary components of work enclosure 112 include a sidewall 136, a bottom closure 140 and a spray nozzle 144. In the example shown, the opening formed by sidewall 136 at upper end 128 of work enclosure 112 is larger than the diameter of spray nozzle 144. Consequently, this example includes a top closure 148 to close the region between nozzle 144 and sidewall 136 so as to prevent backspray from exiting upper end 128 of work enclosure 112. In other embodiments, the upper end of the sidewall and corresponding spray nozzle may be designed so that the interface between the nozzle and sidewall obviates the need for any additional closure at the upper end of the work enclosure. Sidewall 136 includes a "digit" portal 152 ("digit" referring to the digits of a human hand, i.e., the fingers and thumb) that allows a user to insert one thumb or four fingers into the interior of work enclosure 112 in a proper manner (see below). Further details of work enclosure 112 are described below in connection with FIGS. 2-4.

Figure 2:
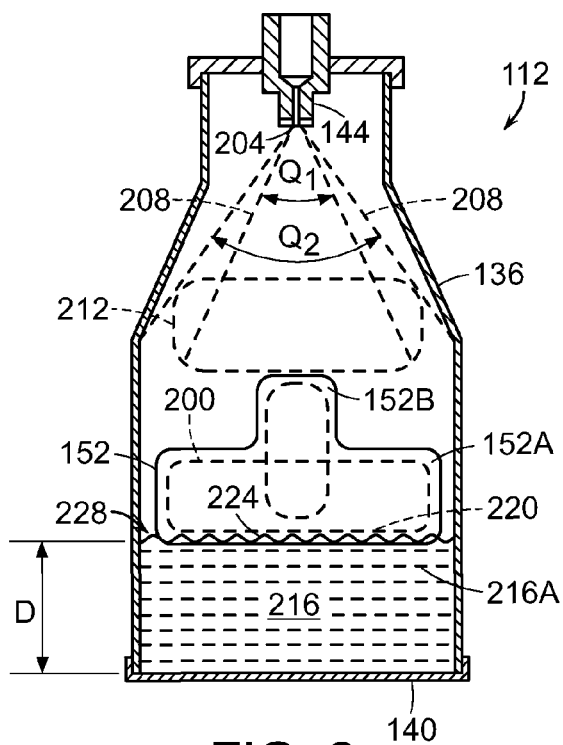
FIG. 2 is an enlarged vertical cross-sectional view of the work enclosure of the water-powered hand-washing system of FIG. 1.

Referring now to FIG. 2, work enclosure 112 is configured to receive the proximal, intermediate and distal phalanges of all four fingers simultaneously so that these four fingers can be cleaned substantially simultaneously with one another. To facilitate this simultaneity, digit portal 152 includes a laterally elongate finger-receiving slot 152A sized to accommodate these four fingers up to and including their proximate phalanges when these fingers are in loose contact with one another and inserted into work enclosure 112 in an upwardly curled manner as illustrated by finger 300 in FIG. 3. In this work position, the intermediate and distal phalanges of these four fingers are wholly contained within work enclosure 112. It is noted that in alternative embodiments in which all three phalanges of all four fingers may be inserted into the work enclosure at once, the work enclosure may be configured so that the user inserts his hand more than or less than shown in FIG. 3. For example, in some other embodiments the work enclosure may be configured for the user to insert their hand up to or past the metacarpophalangeal joints of those four fingers. Some other embodiments may be configured for the user to insert those four fingers only to their intermediate phalanges or their proximal interphalangeal joints.

Figure 3:
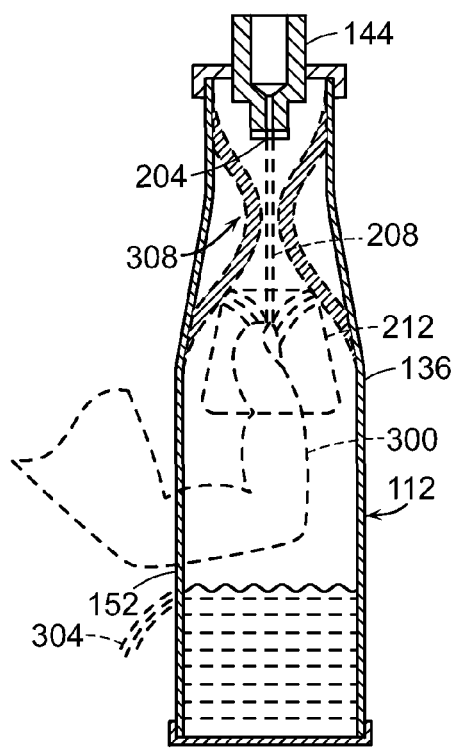
FIG. 3 is an enlarged vertical cross-sectional view of the work enclosure of FIG. 1 illustrating an orientation of a finger inserted into the work enclosure for cleaning.

Referring back to FIG. 2, dashed line 200 indicates the periphery of the approximate space occupied by the portion of the hand (here, the proximal phalangeal portion) that extends through digit portal 152 when an adult hand of 95-percentile breadth (e.g., 3.9 in. (9.8 cm) based on U.S. statistics) is properly positioned relative to work enclosure 112. In the example of FIGS. 1-3, when the four three-phalanx fingers of one of the user's hands are inserted in an upwardly curled manner as illustrated in FIG. 3, the user may be holding work enclosure 112 with the opposite hand by, for example, grasping the necked-down upper portion of the enclosure with the thumb and index and middle fingers. In alternative embodiments, the work enclosure could be secured to a fixture (not shown) or freestanding.

Spray nozzle 144 is either designed or selected to provide high volumetric flow rates and high outlet velocities across a range of delivery pressures. In the example shown, spray nozzle 144 has an outlet orifice 204 configured to provide a fan-shaped spray pattern 208, which is an effective shape because of the generally linear arrangement of the tips of the four three-phalanx fingers when they are in their work position as described above. The magnitude of included-angle θ (theta) may be selected based on the distance of the fingertip-receiving region (denoted by its outline 212) within work enclosure 112 from spray nozzle 144 (here, about 1.5 inches to 2 inches). The four fingers, once inserted, are moved side-to-side (here, about 0.75 inches to about 1 inch) to expose all surfaces to the full force of the high-velocity, high-flow-rate stream from spray nozzle 144. Based on the configuration of work enclosure 112 and working position of the hand within the enclosure, an acceptable included angle θ would generally fall in a range of about 30° ($\theta_1$) to about 60° ($\theta_2$). In other embodiments having configurations different from the configuration of work enclosure 112, the included angle of the corresponding spray patterns may be outside the range shown.

As seen in FIG. 3, in the direction perpendicular to the fan shape, spray pattern 208 remains fairly concentrated. That is, spray pattern 208 has very little spread as the spray moves away from outlet orifice 204. This narrowness allows the force of the spray to be as concentrated as possible in the fingertip-receiving region 212 where the user's digit tips will be located during cleaning. With spray pattern 208 remaining fixed and being relatively narrow in a plane perpendicular to the planes in which the fingers are positioned while present inside work enclosure 112 (i.e., the vertical plane into and out of the page containing FIG. 3), it can be appreciated that for the user to achieve the best cleaning results the user should slowly flex and extend the fingers and move them side-to-side (again, about 0.75 inches to about 1 inch in this example) to expose palmar surfaces, fingernail beds, cuticular regions and lateral surfaces to the spray for an effective amount of time (such as 30 seconds to 40 seconds or more).

Figure 4:
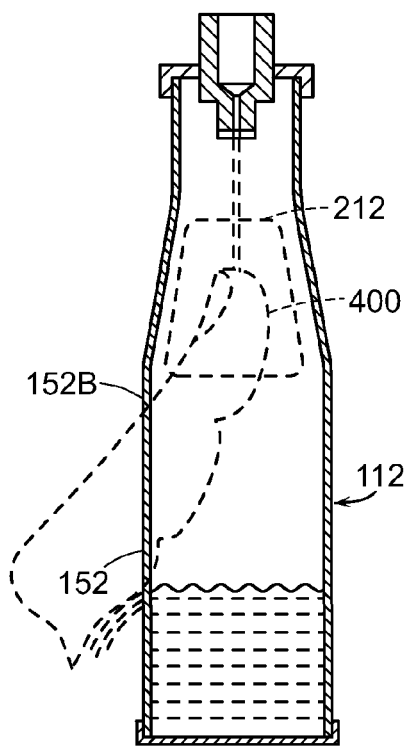
FIG. 4 is an enlarged vertical cross-sectional view of the work enclosure of FIG. 1 illustrating an orientation of a thumb inserted into the work enclosure for cleaning.

Referring again to FIG. 2, and also to FIG. 4, this example of digit portal 152 further includes a thumb notch 152B designed to accommodate the user's thumb 400 (FIG. 4) during washing. FIG. 4 illustrates one way that the user can insert thumb 400 into work enclosure 112, i.e., with the thumbnail generally facing the "front" of the work enclosure. Alternatively, the thumb may be inserted with the thumbnail facing the "back" of work enclosure 112. In either position the thumb can be gently flexed or extended to provide thorough exposure of the palmar surface, fingernail bed, cuticular surface and lateral surfaces to the spray for an effective amount of time (e.g., 20 seconds total or more). The choice of thumb orientation will generally depend on factors such as the location/locatability of work enclosure 112 relative to the user during washing and whether or not the user is holding the work enclosure with the opposite hand during washing.

With thumb 400 being generally more limited in terms of range-of-motion and positionability relative to the three-phalanx fingers, thumb notch 152B allows the user to position the tip of the thumb in fingertip-receiving region 212 where the tips of the three-phalanx fingers are located during washing. When thumb 400 is inserted into work enclosure 212 as shown in FIG. 4, the particular configuration of this work enclosure has roughly the entire distal phalanx of the thumb located within the enclosure. In other embodiments, it may be necessary to design the work enclosure so that some or most of the proximal phalanx of thumb 400 is also located within the enclosure. When thumb 400 of the user's one hand is inserted into work enclosure 112 as shown in FIG. 4, the user may be holding the work enclosure with the other hand, for example, as described above relative to the washing of the four three-phalanx fingers. Alternatively, work enclosure 112 may be secure to a fixture or free-standing.

As mentioned above, a hallmark of a water-powered hand-washing system of the present disclosure is the exposing of finger tips, especially the palmar surfaces, fingernail beds and cuticular regions, to high-impact-energy, high-flow-rate water spray. To this end, in a particular example suited for the particular configuration of working enclosure 112 shown in FIGS. 2-4 (with the various figures being largely in scale relative to finger 300 and thumb 400 of FIGS. 3 and 4, respectively), spray nozzle 144 is standard fan nozzle model ¼"NF1530 (30° fan) available from BETE Fog Nozzle, Inc., Greenfield, Mass. The ¼"NF1530 nozzle has the performance characteristics appearing in the following Table.

TABLE

Performance Characteristics of BETE 30°
Fan Nozzle Model ¼"NF1530

| Inlet Pressure (P) (PSI) | Outlet Flow (Q) (GPM) | Exit Velocity (V) (ft/s (FPS)) | V/Q ((FPS)/(GPM)) |
|---|---|---|---|
| 10 | 0.75 | 34.7 | 46.3 |
| 20 | 1.06 | 49.0 | 46.2 |
| 30 | 1.30 | 60.1 | 46.2 |
| 40 | 1.50 | 69.4 | 46.3 |
| 50 | 1.68 | 77.5 | 46.1 |
| 60 | 1.84 | 85.2 | 46.3 |

The performance characteristics of the BETE® ¼"NF1530 spray nozzle listed in the preceding Table provide hand-washing system 100 (FIG. 1) with very good cleaning performance. Observations of test users have revealed that, with the BETE® ¼"NF1530 nozzle, its spray at an inlet pressure of about 20 PSI is well-tolerated by children. Adult test users have found its spray at about 35 PSI to about 50 PSI to be comfortable and invigorating. In this connection, it is noted that mixing/flow control valve 108 allows users to adjust the spray output by spray nozzle 144 to a comfortable, yet effective level, generally between about 10 PSI (0.75 GPM for the BETE® ¼"NF1530 nozzle) to about 58 PSI (1.8 GPM for the BETE® ¼"NF1530 spray nozzle (again, 1.8 GPM is the current maximum flow rate under California standards)). Operation at pressures higher than 58 PSI with the BETE® ¼"NF1530 spray nozzle is possible depending on code regulations (such as the 2.5 GPM maximum in U.S. states other than California) and whether a particular user can tolerate the resulting higher spray velocities.

As mentioned above, the cleaning effectiveness of hand-washing system 100 is due in large part to dilution and debridement accomplished by subjecting the target digit(s) to both high water flow (dilution) and high-impact water velocity (debridement). Regarding water flow rates, it is desired that the flow rate be at least about 0.75 GPM and more preferably at least about 1.3 GPM, with values up to 1.8 GPM (California standard) or 2.5 GPM (non-California states' standard) typically being more desirable as long as the resulting higher velocities are tolerable by a particular user. Regarding nozzle exit velocity, which correlates with impact force of the spray upon the digit(s) placed in fingertip-receiving region 212 (FIGS. 2-4), it is desirable that the exit velocity be at least about 40 feet per second (FPS) during cleaning, regardless of outlet flow rate or inlet pressure. For adults having the digit closest to the exit orifice of nozzle 144 about 1.5 inches to 2 inches from exit orifice 204, the exit velocity is more preferably at least about 60 FPS.

A convenient way to express the relationship between exit velocity (V) and outlet flow (Q) for any nozzle is to calculate the V/Q ratio. As seen from the Table above, for the BETE® ¼"NF1530 spray nozzle the V/Q ratio is largely constant, here about 46.3 FPS/GPM, over the range of inlet pressures appearing in the Table. It is recognized that water spray nozzles suitable for use as nozzle 144 other than the BETE® ¼"NF1530 nozzle will have performance characteristics different from the performance characteristics of the ¼"NF1530 nozzle presented in the Table above. For example, not only can the V/Q ratio be different, but the outlet flow rates Q and exit velocities at particular pressures can be different, too. For example, a suitable alternative nozzle may provide a flow rate of 1.6 GPM at 30 PSI and have a corresponding outlet velocity of 70 FPS (here, V/Q would be about 43.8 FPS/GPM. Regardless of the nozzle used, it is beneficial for the V/Q ratio, when V is expressed in FPS and Q is expressed in GPM, to be at least about 20 FPS/GPM and more preferably at least about 30 FPS/GPM.

When hand-washing system 100 (FIG. 1) is operating within the intended ranges of flow rates and velocities, the water output of nozzle 144 can be equated to output of a conventional garden-hose nozzle outputting 1.8 GPM in a fairly tightly focused pattern at a line-pressure of 45 PSI. As one can imagine, the output rate and forcefulness of spray nozzle 144 is quite substantial, especially for a device intended for use inside homes, in commercial kitchens and in surgical scrub areas, among other places. In this connection and referring again to FIG. 2, work enclosure 112 includes an energy-dissipation region 216 that, during use, defines an energy-dissipating reservoir of water 216A for rapidly dissipating energy in the high-velocity water spray from nozzle 144 during use, both when one or more digits are properly inserted into the work enclosure and being washed and when the nozzle is spraying water without any digits present within the work enclosure. The latter situation can occur if the nozzle is still operating but the user does not have any digits inside enclosure 112, such as just before or just after a washing operation.

As seen in FIG. 2, dashed line 220 indicates that when a hand is properly engaged with work enclosure 112, a gap exists between the lower edge 224 of sidewall 136 and the hand-occupied region of digit portal 152. FIG. 3 illustrates that when hand-cleaning system 100 is operating, this configuration allows reduced-energy water 304 to fairly gently exit work enclosure 112 and fall to a suitable location, such as a sink, for example, sink 156 of FIG. 1, without interfering with the insertion or removal of any of the digits during a cleaning operation. It is noted that in alternative embodiments, bottom closure 140 and/or sidewall 136 near lower end 132 can each be provided with one or more apertures to partially or fully handle the outflow of water from within work enclosure 112 during use. That said, for the sake of easily maintaining the cleanness of work enclosure 112, the fewer apertures, especially relatively small apertures having reentrant corners/small radii, the better, since contaminants tend to build up in such areas, even with moderate cleaning.

A large part of the energy-dissipation capability of energy-dissipation region 216 is due to the depth D of the pool 228 of water that eventually collects in the energy-dissipation region. Depth D should be great enough that the force of the spray striking pool 228 at full spray without any digits present within enclosure 112 does not part water 228 all the way to bottom closure 140. For the BETE® 30° ¼"NF1530 nozzle described above, an adequate depth D that provides ample energy dissipation is about 1.5 inches. Somewhat lesser depths could likely be tolerated, as could greater depths. If additional apertures are provided to work enclosure 112 as mentioned above, care should be taken to avoid placing them in the direct path of spray pattern 208 if they are un-baffled because the spray will tend to exit the work enclosure forcefully through such apertures until enough depth has built up in pool 228.

FIG. 3 illustrates two configurations of sidewall 136 near spray nozzle 144. The first configuration (shown in solid lines) is a straightforward configuration that includes a gentle tapering of sidewall 136 from its widest region (relative to the view of FIG. 3) near digit portal 152 to its narrowest region near nozzle 144. The second configuration (shown in dashed lines) includes a "pinched" region 308 near nozzle 144 that inhibits backsplashing from the impact of the spray issued by the nozzle upon one or more digits present in fingertip-receiving region 212. By inhibiting such backsplash, contamination of nozzle 144 and regions immediately surrounding the nozzle can be reduced.

Further regarding the cleanness of work enclosure 112, several features of this enclosure provide it with excellent cleanability. In surgical and other patient-care settings, it is likely that work enclosure 112 will be sterilized between uses or top closure 148 with nozzle 144 and the female portion of quick-disconnect assembly (160) will be sterilized and the lower work enclosure (here, sidewall 136 and bottom closure 140) disposable. In the home setting there are several features that facilitate disassembly and cleaning, including: 1) readily removable bottom and top closures 140, 148 (FIG. 1); 2) smooth interior to sidewall 136 that contains few, to no, reentrant corners and other contaminant-trapping structures; 3) simply shaped sidewall that allows easy access to all internal surfaces of the sidewall by, for example, a bottle brush and 4) simply shaped internally facing surfaces of the bottom and top closures.

Regarding materials of construction of the various components of work enclosure 112, each of the components may be made of any material(s) suitable for that component. For example, sidewall 136 may be made of metal, plastic or composite, or any combination thereof, as may be bottom and top closures 140, 148. Likewise, nozzle 144 may be made of metal, plastic or composite, or any combination thereof. Considerations for selecting materials include strength, weight, durability and cost, among others.

Referring again to FIG. 1, in this example hand-washing system 100 includes a quick-disconnect assembly 160 and a shutoff valve 164 that provide the system with great flexibility. The combination of these two elements allows work enclosure 112 to be quickly and easily coupled to and decoupled from flexible conduit 116 for any of a variety of reasons without having to change the setting on mixing/flow valve 108. For example, if hand-washing system 100 includes a second work enclosure, such as child-sized work enclosure 168 (whereas work enclosure 112 is an adult-sized work enclosure), a user could readily switch between the differing work enclosures. In this example, it is noted that work enclosure 168 has all of the features of work enclosure 112, but is sized for smaller hands, such as hands of young children.

Quick-disconnect assembly 160 can be any suitable quick-disconnect assembly, such as a quick-disconnect assembly that includes a suitable combination of male and female couplings, for example, the male and female quick-disconnect couplings available from McMaster-Carr, Atlanta, Ga. Those skilled in the art will readily appreciate that the variety of quick-disconnect couplings is large and the choice of these couplings will depend on things such as the configuration of nozzle 144 (e.g., interiorly, exteriorly threaded, barbed, etc.), the configuration of the immediately adjacent upstream component (here, shutoff valve 164) (e.g., interiorly, exteriorly threaded, barbed, etc.) and design choice.

Similarly, shutoff valve 164 can be any suitable shutoff valve, such as a simple ball valve or stop cock. In other, more elaborate embodiments, the shutoff valve (if provided) can be a lever-type valve of the type commonly found on commercial kitchen utility spray assemblies adjacent the spray heads. An example of such a spray valve having a lever-type valve is the FIS-2946 spray valve available from Fisher Manufacturing Company, Tulare, Calif. It is noted that shutoff valve 164 need not be provided. In such embodiments, if having a water shutoff feature independent of mixing/flow valve 108 is desired, for example, for swapping work enclosures 112, 168 with one another, a type of quick-disconnect valve that shuts off flow when the male and female components are disconnected from one another may be used.

Figure 5:
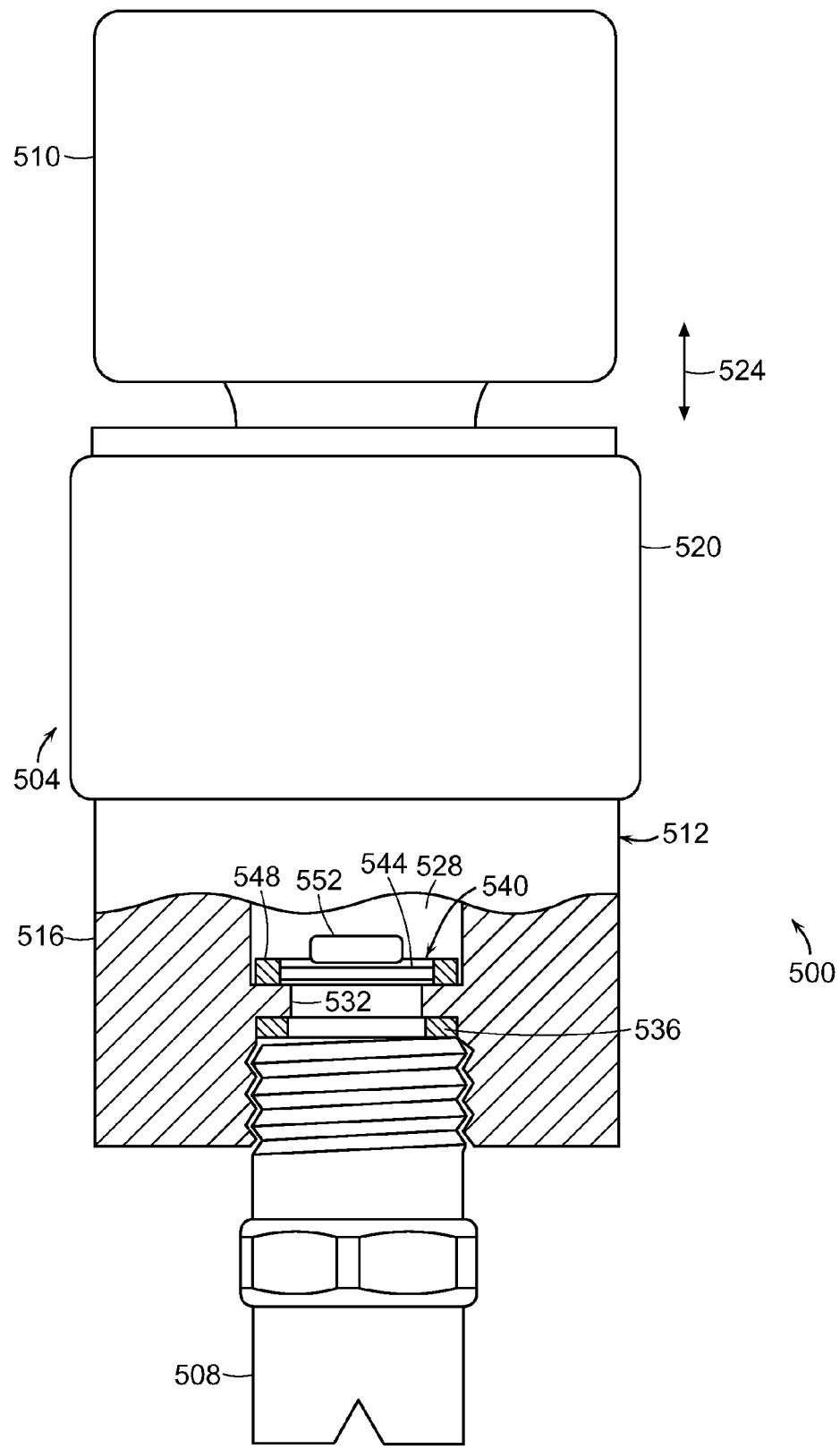
FIG. 5 is an enlarged partial cross-sectional view/partial elevational view of a quick-disconnect coupler/nozzle assembly configured to receive a pill for dispensing a washing agent to a work enclosure of a water-powered hand washer, such as either of the work enclosures of FIG. 1, when the assembly is coupled to such an enclosure.

FIG. 5 illustrates a particular quick-disconnect assembly/nozzle arrangement 500 that can be used with a work-enclosure made in accordance with the broad concepts described above, such as either of work enclosures 112, 168 of FIG. 1. Quick-disconnect assembly/nozzle arrangement 500 allows a user to enhance the cleaning performance of a hand-washing system of the present invention by dispensing a washing agent (e.g., soap, detergent, sanitizer, etc., and any combination thereof) into the water flow that reaches the user's digit(s) present in the work enclosure (not shown). In this example, quick-disconnect assembly/nozzle arrangement 500 comprises a quick-disconnect assembly 504 and a spray nozzle 508. Quick-disconnect assembly 504 includes a male coupling 510 and a female coupling 512 that removably engage one another in a conventional manner. In this example, female coupling 512 includes a body 516 and a sleeve 520 that is movable longitudinally relative to the body. When a user desires to uncouple male and female couplings 508, 512 from one another, the user moves sleeve 520 in the appropriate direction so as to initiate the disengaging process. Arrows 524 indicate the directions of movement of male coupling 510 during engagement and disengagement of the male coupling relative to female coupling 512 (assuming female coupling is fixed in space). Alternatively, some designs permit uncoupling to be initiated by a convenient button on the side of the female component. The Standard Push-Button Socket model no. 5163T11, available from McMaster-Carr, displays this feature.

In this example, body 516 of female coupling 512 includes a longitudinal central passageway 528 and an integral annular stop 532. Stop 532 provides a first shoulder for engaging a sealing gasket 536 between female coupling 516 and spray nozzle 508 and a second shoulder for engaging a screen assembly 540. Here, screen assembly 540 includes a screen 544 and an annular resilient gasket 548 that has a slight interference fit with passageway 528 so as to hold the assembly in place within the passageway. In this example, the washing-agent dispensing feature is implemented by a user inserting a washing-agent pellet or pill 552 into passageway 528 upstream of screen assembly 540. It is noted that the word "pill" is used herein and in the appended claims for convenience to denote both a self-contained mass of one or more pure washing agents and a self-contained mass of one or more pure washing agents in combination with one or more fillers, one or more binding agents, one or more additives, and/or a containment structure (e.g., a gel capsule), and any combination thereof. Pill 552 should have an appropriate shape that does not significantly impact the flow rate through female coupling 516.

In a typical scenario, a user inserts washing-agent pill 552 into passageway 528 by disengaging male coupling 510 from female coupling 512, places the pill into the passageway and re-engages the male coupling with the female coupling. During operation of the hand-washing system of which quick-disconnect assembly/nozzle arrangement 500 is made a part, water (not shown) flowing through passageway 528 slowly dissolves washing-agent pill 552 and causes the output (not shown) of spray nozzle 508 to contain the dissolved portion of the pill. In one embodiment, pill 552 is designed to dissolve in an amount of time equal to, or roughly equal to, the amount of time anticipated for a typical wash cycle, either for one hand or both hands, as desired. Other types of washing-agent dispensing arrangements are possible, such as an arrangement that uses a venturi eductor to draw a washing agent into the water flow before it is ejected into the work enclosure. Those skilled in the art will understand how to provide such alternative washing-agent dispensing arrangements to a hand-washing system made in accordance with the present disclosure.

In the above described embodiment, water, alone or in combination with other washing agent (e.g., soap, detergent, sanitizer, etc.), is used for cleaning the digits of the human hand. In other environments, other anti-microbial agents can be substituted for water. For example, AMOSILQ is an anti-microbial comprised of a quaternary ammonium organosilicate for forming a chemical bond that will kill (lyse) all microorganisms (bacteria, spore-forming bacteria, enveloped and nonenveloped viruses and fungi) that come in contact with it for a period of at least 6 months.

Referring again to FIG. 1, in certain applications, all surfaces of the work enclosure 112 can be treated with an anti-microbial agent such as AMOSILQ.

Figure 6:
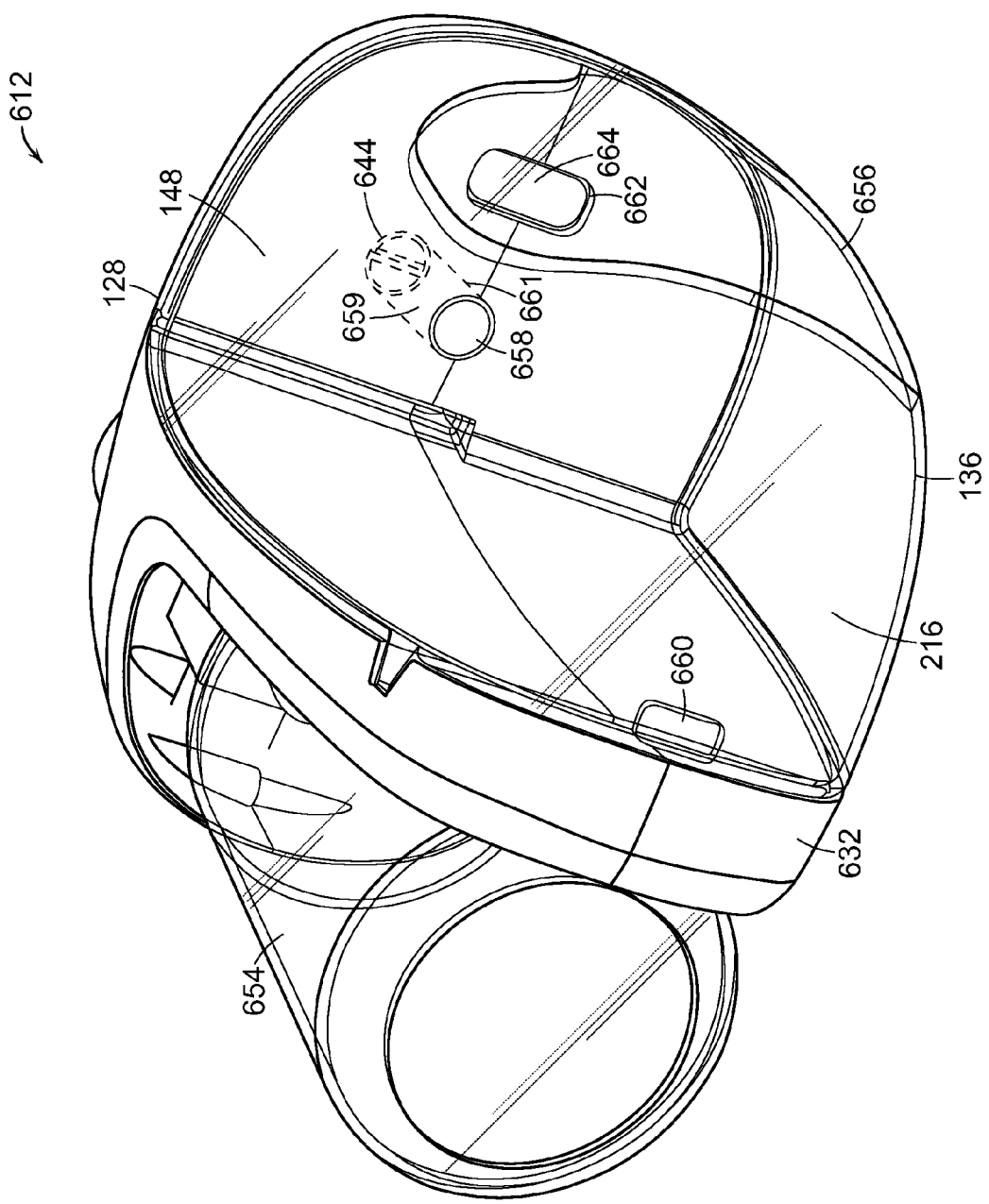
FIG. 6 is a view of an alternative embodiment of a work enclosure of a water-powered hand-washing system.

Referring to FIG. 6, an alternative embodiment of the work enclosure 612 includes three apertures. In this alternative embodiment, work enclosure 612 includes aperture 656, which serves as a digit portal positioned on the side of the work enclosure 612 and is configured to accommodate a user's fingers and thumb during washing. The first aperture 656 has substantially the same size and shape as the digit portal 152 of work enclosure 112 of FIG. 1.

A second aperture 658 of the three apertures is positioned substantially at an inner surface of the top closure 148 of the work enclosure 612 and opens into a recessed channel 659. The recessed channel 659 extends from the inner surface of the top closure 148 and in a direction toward the top end 128 of the work enclosure 612. The recessed channel 659 is terminated by the spray nozzle 644. The second aperture 658 and the recessed channel 659 are configured to avoid contamination of the spray nozzle 644 and an inside surface 661 of the recessed channel 659 by preventing deflected spray from the digits, possibly containing microbes, from reaching the spray nozzle 644 and the inside surface 661 of the recessed channel 659 during washing. In some examples, the recessed channel 659 has a length of ½ inch.

For example, if the water sprayed from the spray nozzle 644 flows with sufficient force (e.g., 70 ft/sec) and with sufficient volume (e.g., 1.5 gal/min) it will likely fill the recessed channel 659. With the recessed channel 659 filled, little to no deflected spray is able to enter the recessed channel 659 to contaminate the inner surface 661 of the recessed channel 659 or the spray nozzle 144. In this way, cross contamination at the site of greatest concentration of displaced microbes (i.e., the top of the work enclosure 612) is avoided.

A third aperture 660 of the three apertures is positioned at the lower end 632 of the work enclosure 612 and is configured to allow water to evacuate the work enclosure 612. In some examples, the third aperture 660 is sized such that, during washing, the rate of water evacuating the work enclosure 612 is less than the rate of water being sprayed into the work enclosure 612 by the spray nozzle 644. In this way, the energy dissipation region 216 of the work enclosure 612 fills with water during washing, thereby absorbing deflected spray and microbes. When washing ends and the spray nozzle 644 is turned off, the water in the dissipation region 216 of the work enclosure 612 quickly evacuates through the third aperture 660. In some examples, any water that is retained in the work enclosure 612 after evacuation is reduced to a thin film which efficiently presents all microbes in the retained water to an AMOSILQ layer that has been chemically bonded to the plastic surface of the interior. Once presented to the AMOSILQ layer, the outer structure of the microbes is lysed and the organisms destroyed.

In some examples, the dimensions of the third aperture 660 are determined by the rate of evacuation of water from the work enclosure 612 once the spray nozzle 644 is turned off. In some examples, the dimensions of the third aperture 660 are configured such that substantially all of the water is evacuated from the work enclosure 612 in approximately five seconds. In other examples, the dimensions of the third aperture 660 are configured such that substantially all of the water is evacuated from the work enclosure 612 within a range of two to ten seconds.

In some examples, the work enclosure 612 described above is fully assembled and sterile-packaged. In some examples, the work enclosure 612 is easily interchangeable in the water-powered hand-washing system. In some examples, the third aperture 660 is positioned such that it is not directly in the path of the spray pattern of the spray nozzle 644, thereby avoiding spray forcefully exiting the work enclosure 612 before the dissipation region 216 fills with water.

In some examples, rather than using a washing agent pill or pellet to dispense washing agents (as is described above in relation to FIG. 5), a bottle of washing agent 654 is included in the work enclosure 612. Water entering the work enclosure 612 is mixed with the washing agent from the bottle 654 before being forced through the spray nozzle 644.

In some examples, the work enclosure 612 includes a presence sensor recess 662 which includes, for example, a translucent plastic window 664 behind which a presence sensor (not shown) is positioned. In some examples, if the presence sensor detects the presence of a user's digits in the work enclosure 112, the water-powered hand-washing system 100 is activated for a predetermined and adjustable amount of time. In some examples, the presence sensor is an infrared beam which shines through the window 664 and, when broken, indicates the presence of the users' digits in the work enclosure 612. In general, any suitable type of presence or proximity sensor can be used to detect that the user's digits are present in the work enclosure.

In further embodiments described below, a version of the water-powered hand-washing system is described for accommodating all ten fingers/digits including eight fingers and two thumbs of both left and right hands simultaneously, thus providing a ten fingered power washer (TFPW).

Figure 7:
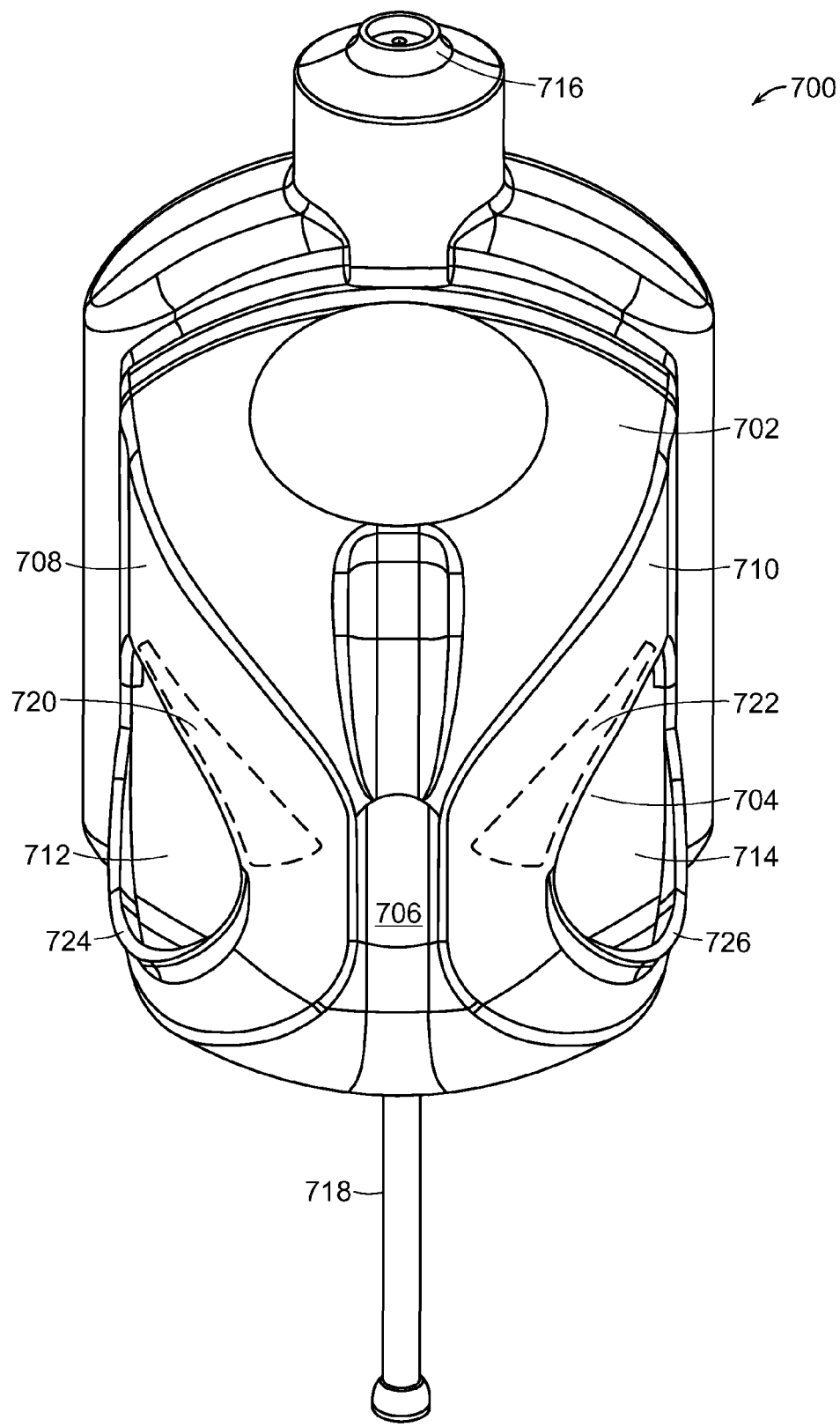
FIG. 7 is a front perspective view of an alternative embodiment of a two hand work enclosure of a water-powered hand-washing system according to this invention.

As shown in FIG. 7, a hand washing apparatus 700 includes an enclosure 702 having an interior space 704. With this embodiment both hands and all ten (10) digits/fingers including under the nail beds of the fingers can be washed simultaneously. The enclosure includes a front face 706 and left and right side faces 708 and 710 in which are included two openings, 712 and 714, allowing access to the interior space 704 through which a user can insert her left and right hand, respectively, for cleaning There is an inlet 716 which is adapted to be connected to a faucet through which water will flow ultimately to spray nozzles (not shown) for washing the user's hands. The waste water then exits the enclosure through a drain (not shown) in the bottom of the interior space 704 and then through drain pipe 718, which can also function as an adjustable stand to aid in the support and stabilization of the unit so not to place undue fatigue on the faucet spout.

The left and right side faces 708 and 710 and the two openings 712 and 714 are disposed at angles relative to front face 706 to allow for comfortable ingress and egress of the hands and proper placement within interior space 704. In addition, the openings 712 and 714 have inwardly curled lips 720 and 722 on the upper portion of the openings and outwardly curled lips 724 and 726 on the lower portion of the openings to reduce spray leakage onto the wrists and shirt cuffs of the user.

Figure 8:
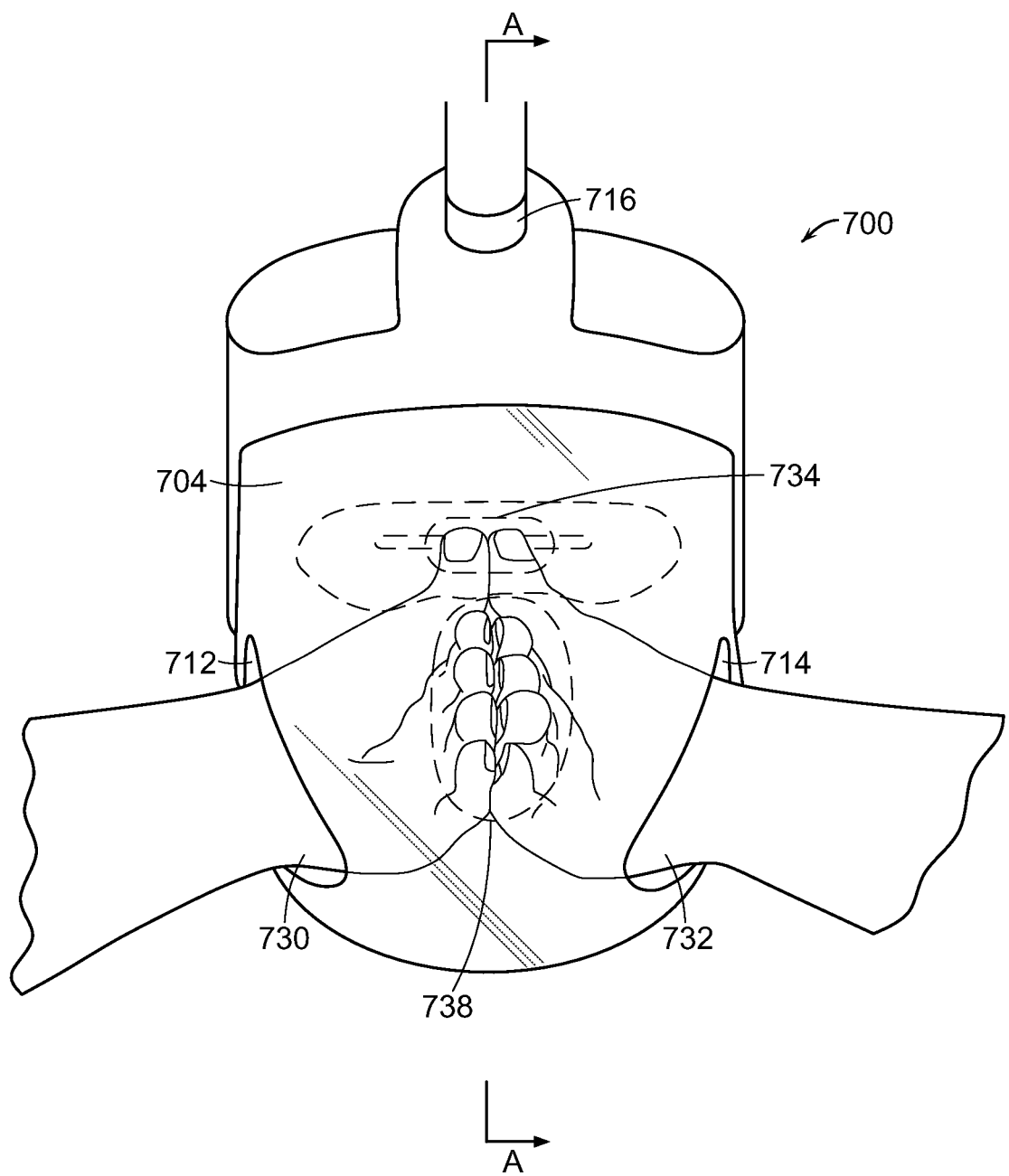
FIG. 8 is another front perspective view the two hand work enclosure of a water-powered hand-washing system of FIG. 7.

As shown in FIG. 8, left hand 730 is inserted through left opening 712 and right hand 732 is inserted through right opening 714 into interior space 704. The two openings are angled to comfortably position the digits in a generally upwardly directed fashion in interior space 704 with the nail beds of a subset of fingers/digits 734, namely the thumbs, being directed toward the rear surface of interior space 704 and facing a spray nozzle (not shown). Another subset of fingers/digits 738, namely the three-phalanx fingers or all fingers excluding the thumbs, being directed toward the top and front surfaces of interior space 704 and facing another spray nozzle (not shown).

Figure 9:
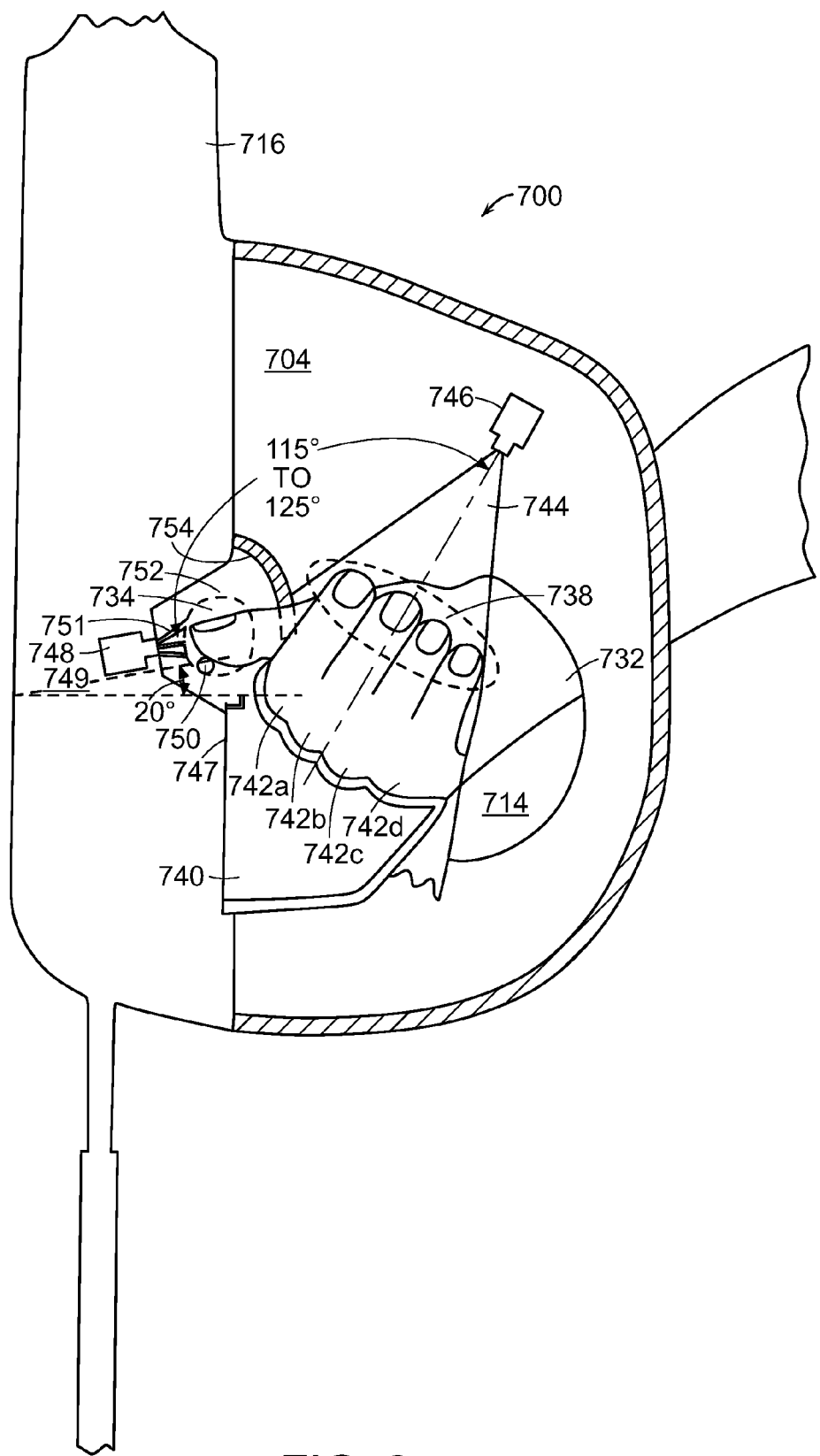
FIG. 9 is a cross sectional view of the two hand work enclosure of a water-powered hand-washing system of FIGS. 7 and 8 taken alone line A-A.

As shown in FIG. 9, a cross-sectional view of enclosure 702 taken along line A-A of FIG. 8 such that only right hand 732 and its digits are visible. Hand 732 is placed on digit support member 740 with the knuckles of the three-phalanx fingers placed in semi-circular recesses or indentations 742a-d to enable proper placement of the subset of fingers 738 in the direct path of spray 744 being directed from spray nozzle 746. Digit support 740 may be configured as a single support to accommodate the knuckles of both hands or may be configured as two separate supports, one for each hand.

Spray nozzle 746 is a fan nozzle, such as a BETE NF15, that will spray a wide enough swath based on the distance from the fingers with sufficient force to clean under the fingernail beds of the index, middle, ring and little fingers of each hand.

The subset of fingers 734, i.e. the thumbs, are presented facing the rear wall 747 of the interior space 704 in proximity to a spray nozzle 748, which is also a fan nozzle, such as a BETE NF08. A digit support member 750, such as a touch bar including a touch sensor, is used to sense when the user has properly positioned her thumbs for cleaning. In this embodiment the digit support is located within a concave section 752 of rear wall 746.

In addition to enabling proper alignment of the thumbs, digit support member 750 may also be used to allow the user to press the thumbs against it as a means for opening up the nail beds for better access and cleaning by the spray. To accomplish this, digit support member 750 may be provided with a non-slip surface (i.e. increased friction) by applying epoxy paint or by providing a non-slip, machined surface. The increased friction of the surface will allow the user to open up the nail bed during cleaning by pushing on the bar to manipulate the thumb and skin below the nail bed.

Spray nozzle 748 is directed at an upward angle of approximately 20-30 degrees from a plane 749 which is oriented at a 90 degree angle relative to rear wall 746 and emits spray 751 at a sufficient force and appropriate alignment to the nail beds of the thumbs for proper cleaning Spray guard 754 is affixed to rear wall 746 and extends downwardly in close proximity to the users thumbs to block spray 744 from the two spray nozzles 746 and 748.

The nozzle 746 is placed at approximately 115 degrees to 125 degrees from nozzle 748 both nozzles are set at an average approximate distance of 1-2 inches from the tips of the digits/fingers. The nozzles are configured to spray water with predefined outlet flow rates and exit velocities based on predefined inlet pressures as described above with regard to the other embodiments. Exit velocities will affect cleaning efficiency and user comfort. The ability to measure inlet pressures will allow users to repeat what their individual experiences reveal about appropriate pressures for their perceived need in future use of the hand washing apparatus of this invention. Outlet flow rates will allow operation to stay within performance regulations established by states and countries for faucets and showers. It is of note that the hand washing apparatus of this invention used at its maximum volume of 2.5 gpm for 60 seconds will use 2.5 gallons of water, just $\frac{1}{4}^{th}$ the volume required to clean all ten fingers with prior art hand washer systems.

The following data represents the theoretical maximum flow rates of the spray nozzles (BETE NF15 and NF08, for example) typically utilized for this invention:

| Pressure (PSI) | Flow (GPM) |
| --- | --- |
| 20 | 1.63 |
| 30 | 1.99 |
| 40 | 2.3 |
| 60 | 2.82 |
| 80 | 3.25 |
| 100 | 3.63 |

The enclosure will retain its energy dissipation region to capture spray and conduct water and displaced microbes out of the bottom of the unit over the lower rim of the entry portals or a drain hole of appropriate size located in the lowest point of the reservoir. This is described in more detail above with regard to the other embodiments.

Hand washing apparatus 700 may be turned on manually or it may have a touch-less sensor to activate the cleaning cycle for a programmed period of time. The electronic controls may be capable of delivering a solution containing an antimicrobial chemical of controlled concentration to the spray nozzles during part or all of the cleaning cycle. This feature may be accomplished by utilizing the water pressure within the unit to deliver a concentrated solution of the antimicrobial chemical to a reservoir within the hand washing apparatus 700 and subsequently to the nozzles.

Figure 10A:
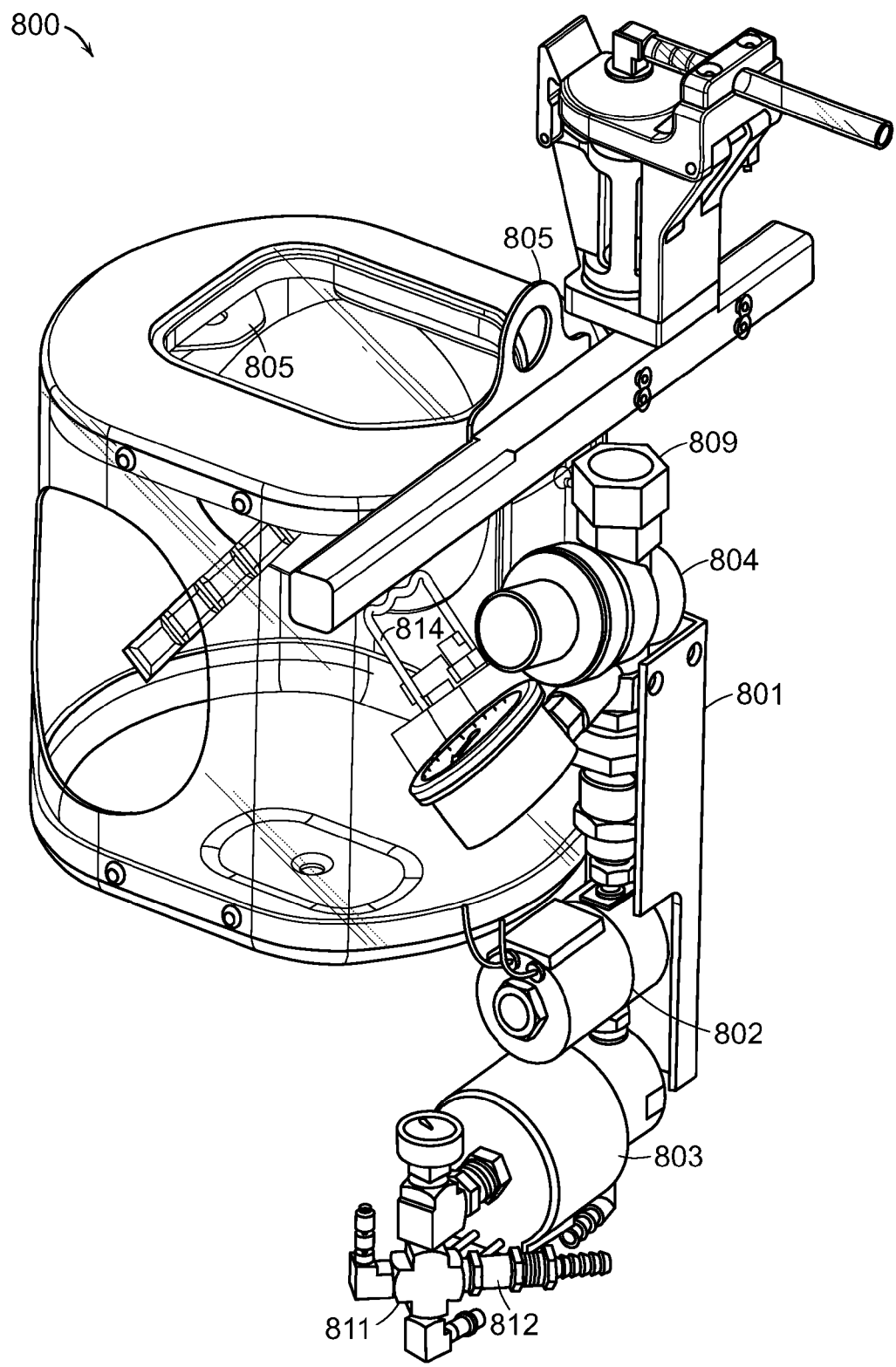
FIG. 10a is a rear isometric rear view of another embodiment of the two hand work enclosure of a water-powered hand-washing system according to this invention.
Figure 10B:
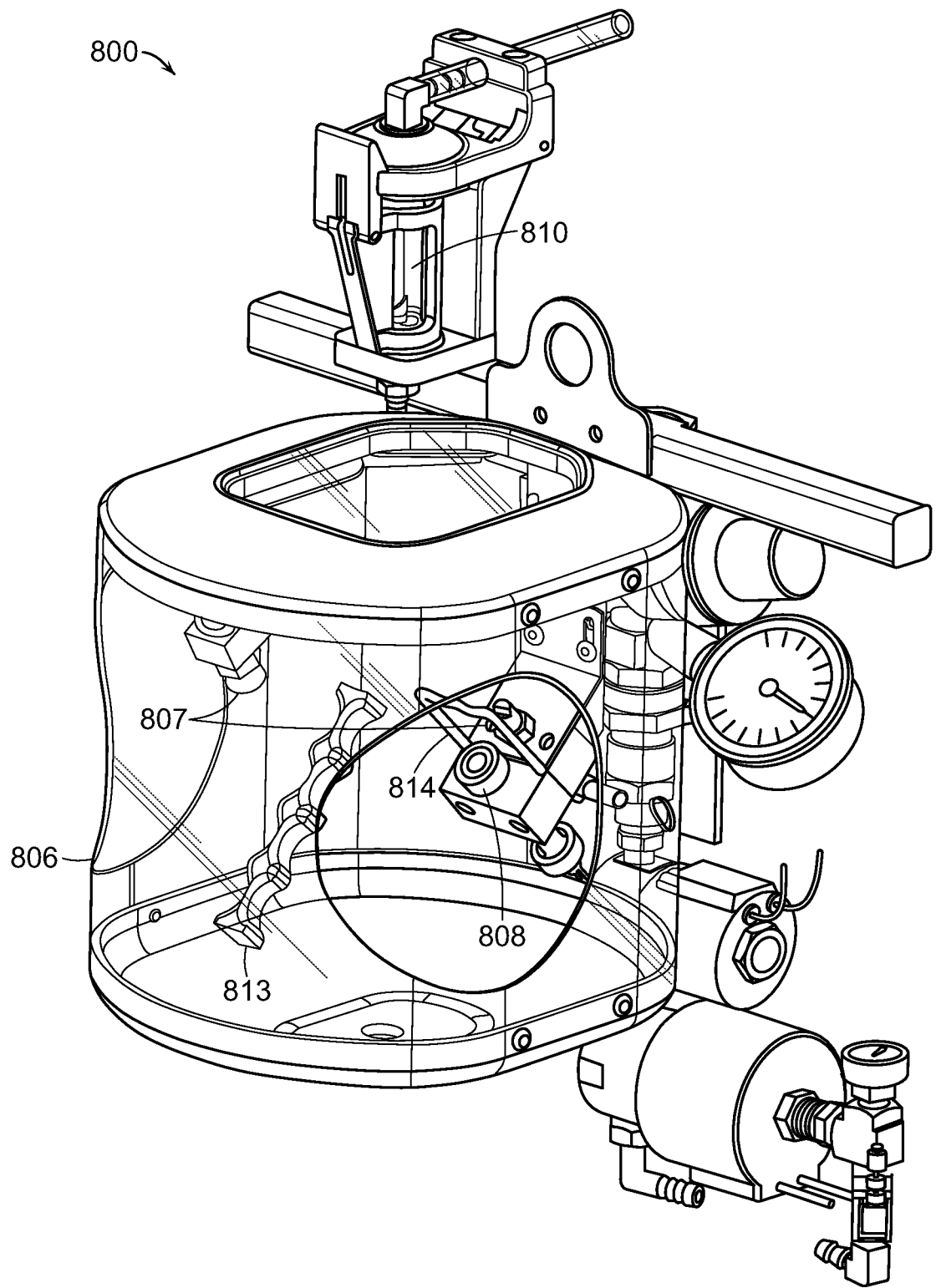

An alternative embodiment of the hand washing apparatus according to this invention is shown as 800 in FIGS. 10a and 10b. The mechanical layout of the hand washing apparatus according to this invention, which can be used for any embodiment of this invention, is also depicted in FIGS. 10a and 10b.

Hand washing apparatus 800 includes a central back bone 801 which rigidly supports valve train 802/803 and regulator/pressure gauge assembly 804. A main-frame 805 supports the housing 806, which includes spray nozzles 807a and b, magnetic initiation switch 808 to activate the hand washing system when the hands are properly positioned, and other internal hardware. Apparatus 800 is affixed to a faucet (not shown) via quick disconnect coupling. The female coupling 809 resides atop the regulator/gauge 804 while the male coupling (not shown) forms part of the faucet.

The first device in the water stream from the faucet is the regulator and gauge 804 and then the main control solenoid valve 802. The main control solenoid valve 802 opens when triggered by the magnetic initiation switch 808 to allow water through the valve train 802/803. The 3-way solenoid valve 803 switches the water flow between two paths; one path delivers pure water while the other path allows the mixing of pure water with an aqueous solution of Amosil-Q antimicrobial liquid contained in canister 810. The two paths rejoin at a tee 811 down-stream of the canister 810 of Amosil-Q. There is a check valve 812 placed in the appropriate location to ensure no back-flow into the canister 810 of Amosil-Q.

In this embodiment the first digit support member takes the form of a digit aligner bar 813, which dictates the proper location/orientation for the user's fingers in relation to the spray stream of nozzle 807a. The digit aligner bar 813 is an element to aid in the optimum positioning and effectiveness for both fingers and thumbs. This element can exist as separate components or be integrated to a single removable unit that can be cleaned separately. The element provides both anterior and posterior contact on the soft skin below the nail beds to aid in opening the underside of the nail to the high pressure fan nozzle spray. The positioning and spreading element has scalloped contact edges to evenly pull back the soft tissue below the nails. These edges may be textured to further aid in the contact grip against the skin. The finger spreading elements are set perpendicular to the finger spraying nozzles. The element includes two opposing side surfaces which each contain four semi-circular recesses or indentations to position the users three-phalanx fingers on each hand in a generally upward direction so that the nail beds are facing spray nozzle 807b.

For clarity sake, digit aligner bar 813 is not shown affixed to housing 806, but can be affixed in a variety of ways which will be apparent to those skilled in the art. In addition, digit aligner bar 813 may be configured as a single bar, as shown, to accommodate the fingers of both hands or may be configured as two separate aligner bars, one for each hand.

A second digit support member takes the form of thumb nail support/spreader 814 which is placed in the front of the thumb spray nozzle 807a to aid in nail bed alignment to the nozzle spray. Nail support/spreader 814 in this embodiment includes a cross bar with two semi-circular recesses or indentations to accommodate the user's thumbs supported by two upright supports emanating from the nozzle housing.

As described above with regard to digit support member 750, FIG. 9, the recesses of the nail support/spreader 814 may be provided with non-slip surfaces (i.e. increased friction) by applying epoxy paint or by providing a non-slip, machined surface. The increased friction of the recessed surfaces will allow the user to open up the nail beds of the thumb nails during cleaning by pushing on the bar to manipulate the thumb and skin below the nail bed.

It should be noted that the digit support members for the three-phalange fingers, namely support member 740 and digit aligner 813 may also be provided with non-slip surfaces (i.e. increased friction) in the recesses/indentations by applying epoxy paint or by providing a non-slip, machined surface. The increased friction of the surface will allow the user to open up the nail beds of the eight fingers during cleaning by pushing on the member to manipulate the fingers and skin below the nail bed.

Figure 11:
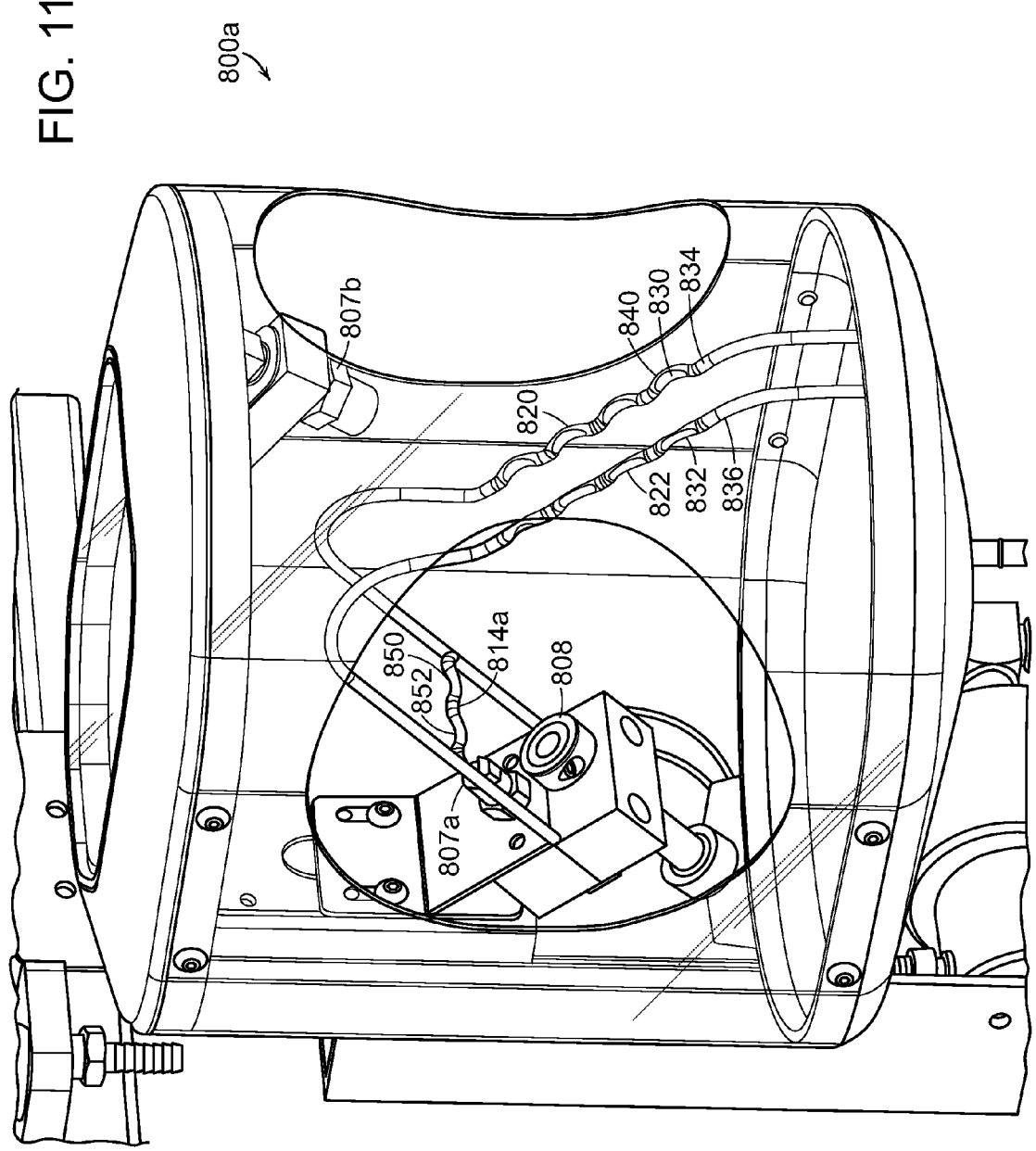
FIG. 11 is a front isometric view of yet another embodiment of the two hand work enclosure of a water-powered hand-washing system according to this invention.

In an alternative embodiment hand washer apparatus 800a, FIG. 11, nail support/spreader 814a is supported by two support bars 820, 822 one on either side of the nail support/spreader. The support bars are affixed at their one ends to the lower surface of the interior of housing 806 and at their other ends to the housing for spray nozzle 807a and magnetic switch 808. The housing for spray nozzle 807a and magnetic switch 808 is angled at approximately 40 degrees relative to the lower surface of the interior region of housing 806. The support bars 820,822 at one end extend perpendicularly from the housing for spray nozzle 807a and magnetic switch 808 toward the upper surface of the interior region of housing 806 and bend at approximately ninety degrees toward the lower surface of the interior region where they are affixed and their other ends.

As shown in FIGS. 11 and 12a, the support bars 820 and 822 have a plurality of recesses 830a-d and 832a-d, respectively, one for a subset of digits, namely, each of the three-phalanx fingers of the right and left hands. Support bar 820 receives the fingers of the right hand and support bar 822 receives the fingers of the left hand. The recesses 830a-d and 832a-d are angled downwardly at approximately 30 degrees relative to a plane formed by the top surfaces 834 and 836 of support bars 820 and 822, respectively, in order to comfortably receive the inner sides (opposite the nails) of each the three-phalanx fingers. The recesses 830 and 832 are formed to fit the fingers and to terminate in sharp, curved knife-edges 844/846, at the intersection of the recesses and roughened, concave surfaces 840 and 842, respectively. As the user places the fingers in the recesses and applies pressure, the knife edges 844/846 become wedged under the nails allowing the nail beds to open up so that they are more exposed for better cleaning.

As more clearly depicted in FIG. 12b, nail support/spreader 814a includes recesses 850 and 852 for receiving the other subset of digits, namely the thumbs of the right and left hands. The recesses 850 and 852 are formed in surface 860 of nail support/spreader 814a which is parallel to a plane formed by the surfaces 862 and 864 of support bars 820 and 822, respectively. The recesses 850 and 852 are formed to fit the thumbs and to terminate in sharp, curved knife-edges 874/876, at the intersection of the recesses and roughened, concave surfaces 870 and 872, respectively. As the user places the thumbs in the recesses and applies pressure, the knife edges 874/876 become wedged under the nails allowing the nail beds to open up so that they are more exposed for better cleaning.

As described above with regard to the other embodiments of the digit support members, the recesses 830, 832, 850, and 852 may be provided with non-slip surfaces (i.e. increased friction) by applying epoxy paint or by providing a non-slip, machined surface.

Hand washing apparatus according to this invention is powered by battery power electromechanical valves and control panel status LED's but may be powered in any other conventional manner.

Exemplary embodiments have been disclosed above and illustrated in the accompanying drawings. It will be understood by those skilled in the art that various changes, omissions and additions may be made to that which is specifically disclosed herein without departing from the spirit and scope of the present invention. It is to be understood that the foregoing description is intended to illustrate and not to limit the scope of the invention, which is defined by the scope of the appended claims. Other embodiments are within the scope of the following claims.

It is noted that various non-limiting embodiments described herein may be used separately, combined or selectively combined for specific applications. Further, some of the various features of the above non-limiting embodiments may be used to advantage without the corresponding use of other described features. The foregoing description should therefore be considered as merely illustrative of the principles, teachings and exemplary embodiments of this invention, and not in limitation thereof.

It is further to be understood that the above-described arrangements are only illustrative of the application of the principles of the present invention. Numerous modifications and alternative arrangements may be devised by those skilled in the art without departing from the scope of the invention, and the appended claims are intended to cover such modifications and arrangements.

What is claimed is:

1. An apparatus configured to simultaneously wash nail beds of both a left hand and a right hand, said apparatus comprising: an enclosure having an exterior surface and an interior space, the exterior surface having a front face and first and second side faces located on opposites sides of the front face; the enclosure comprising: a first opening in the first side face of the exterior surface for receiving a left hand for insertion into the interior space; and a second opening in the second side face of the exterior surface for receiving a right hand for insertion into the interior space; a finger-support member located within the interior space, the finger-support member having a first end, wherein the first end is attached to a lower surface of the enclosure, wherein the finger-support member extends along a first direction toward an upper surface of the enclosure, the finger-support member having a finger-support surface for receiving and orienting fingers of the left hand and fingers of the right hand in a first predetermined position within the interior space, wherein the finger-support surface comprises a first set of recesses to receive the fingers of the left hand, and a second set of recesses to receive the fingers of the right hand; a thumb-support member located within the interior space, wherein the thumb-support member extends along a second direction that is different from said first direction, the thumb-support member having a thumb-support surface for receiving and orienting a thumb of the left hand and a thumb of the right hand in a second predetermined position within the interior space; a finger-spraying nozzle, wherein the finger-spraying nozzle is positioned in the interior space and directed toward the finger-support member at a first predetermined orientation, wherein the finger-spraying nozzle is configured to spray a liquid toward the finger-support member for irrigating fingers received and oriented therein in the first predetermined position when left and right hands are inserted into the interior space of the enclosure; and a thumb-spraying nozzle, wherein the thumb-spraying nozzle is positioned in the interior space and directed toward the thumb-support member at a second predetermined orientation, wherein the thumb-spraying nozzle is configured to spray a liquid toward the thumb-support member so as to irrigate thumbs received and oriented therein at the second predetermined position when left and right hands are inserted into the interior space.

2. The apparatus of claim 1, wherein each of the recesses in the finger-support member includes a surface having a feature to increase friction thereof, wherein said feature is chosen from the group consisting of a coating, and an increased roughness.

3. The apparatus of claim 1, wherein the first and second openings are circular and have curled lip portions angled inward toward the interior space on an upper portion of the openings and curled lip portions angled outward away from the interior space on a lower portion of the openings.

4. The apparatus of claim 1, further including a drain located in a bottom wall of the enclosure for allowing sprayed liquid to be removed from the interior space.

5. The apparatus of claim 1, wherein the interior space of the enclosure includes a top surface, a front surface and a rear wall, wherein the thumb-support member is attached to the rear wall such that when the left thumb and right thumb are positioned on the thumb-support member, the left thumb and right thumb are presented to the thumb-spraying nozzle, and wherein the finger-support member is positioned such that when the fingers of the left hand and the fingers of the right hand are positioned on the finger-support member, the fingers of the left hand and the fingers of the right hand are presented to the finger-spraying nozzle.

6. The apparatus of claim 1, wherein the finger-support member comprises a left finger-support member for supporting fingers of the left hand and a right finger-support member for supporting the fingers of the right hand, wherein the left finger-support member is separate from the right finger-support member.

7. The apparatus of claim 1, wherein the thumb-support member includes a left thumb-support member for supporting the thumb of the left hand and a right thumb-support member for supporting the thumb of the right hand.

8. The apparatus of claim 1, wherein the second direction is substantially perpendicular to the first direction.

9. The apparatus of claim 1, further including a sensor to activate a cleaning cycle when at least one hand selected from the group consisting of the left hand and the right hand is placed in the interior space of the enclosure.

10. The apparatus of claim 9, wherein the sensor is configured to detect that at least one thumb selected from the group consisting of the left thumb and right thumb is positioned on the thumb-support member.

11. The apparatus of claim 1, wherein the surface of the thumb-support member includes a plurality of recesses to receive the thumb of the left hand and the thumb of the right hand.

12. The apparatus of claim 11, wherein the thumb-support member includes a plurality of concave surfaces, each of which is associated with one of the recesses, and wherein a curved edge is formed at an intersection of each concave surface and its associated recess for engaging a thumb.

13. The apparatus of claim 11, wherein each of the recesses in the thumb-support member includes a surface having a feature to increase friction of the surface, wherein said feature is selected from the group consisting of a coating, and an increased roughness.

14. The apparatus of claim 1, wherein the finger-support member orients the fingers of the left hand and the fingers of the right hand in an upward facing direction toward an upper wall of the enclosure and the thumb-support member orients the thumb of the left hand and the thumb of the right hand in a rearward facing direction toward a rear wall of the enclosure.

15. The apparatus of claim 14, wherein the finger-spraying nozzle is located proximate to an upper wall of the enclosure and is directed toward the fingers of the left hand and the fingers of the right hand and wherein the thumb-spraying nozzle is located proximate to a rear wall of the enclosure and is directed toward the thumb of the left hand and the thumb of the right hand.

16. The apparatus of claim 15, wherein the thumb-spraying nozzle is angled at approximately 20 degrees upward relative to a horizontal plane perpendicular to the rear wall and the finger-spraying nozzle is angled at about 115 to 120 degrees from the thumb-spraying nozzle.

17. The apparatus of claim 1, wherein the finger-support member includes a plurality of concave surfaces, each of which is associated with one of said recesses, and wherein a curved edge is formed at an intersection of each concave surface and its associated recess for engaging a finger.

18. The apparatus of claim 17, wherein the edge is a curved knife-edge that is oriented to become wedged under a fingernail so as to expose a nail bed to spraying.

19. The apparatus of claim 17, wherein the finger-support member includes a first surface for receiving fingers of the right hand and a second surface for receiving fingers of the left hand.

20. The apparatus of claim 19, wherein the finger-support member includes first and second support elements, said first support element includes said first surface for receiving fingers of the right hand and said second support element includes said second surface for receiving the fingers of the left hand.

* * * * *